United States Patent [19]

Jarvik

[11] 4,173,796
[45] Nov. 13, 1979

[54] TOTAL ARTIFICIAL HEARTS AND CARDIAC ASSIST DEVICES POWERED AND CONTROLLED BY REVERSIBLE ELECTROHYDRAULIC ENERGY CONVERTERS

[75] Inventor: Robert K. Jarvik, Salt Lake City, Utah

[73] Assignee: University of Utah, Salt Lake City, Utah

[21] Appl. No.: 858,921

[22] Filed: Dec. 9, 1977

[51] Int. Cl.² .................................................. A61F 1/24
[52] U.S. Cl. .................................... 3/1.7; 417/390; 417/389; 417/423 R
[58] Field of Search ......... 3/1.7, 1; 128/1 D, DIG. 3; 417/390, 389, 394, 395, 423 R

[56] References Cited
U.S. PATENT DOCUMENTS

| | | | |
|---|---|---|---|
| 3,568,214 | 3/1971 | Goldschmied | 3/1.7 |
| 3,572,979 | 3/1971 | Morton | 3/1.7 X |
| 3,633,217 | 1/1972 | Lance | 3/1.7 |
| 3,636,570 | 1/1972 | Nielson | 3/1.7 |
| 3,783,453 | 1/1974 | Bolie | 3/1.7 |
| 3,874,002 | 4/1975 | Kurpanek | 3/1.7 |

OTHER PUBLICATIONS

The Development of an Intrapericardial Cardiac Replacement Phase II, by W. H. Burns, et al., Transactions American Society for Artificial Internal Organs, vol. XII, 1966, pp. 272-274.

Primary Examiner—Ronald L. Frinks

[57] ABSTRACT

Total artificial hearts and circulatory assist devices, including left ventricular assist devices. The invention relates to electrohydraulic energy converter systems, whereby electric energy from a power source, which may be a battery or other source, is converted into hydraulic power capable of actuating diaphragm, sack, axi-symmetric or other types of blood pumps.

11 Claims, 12 Drawing Figures

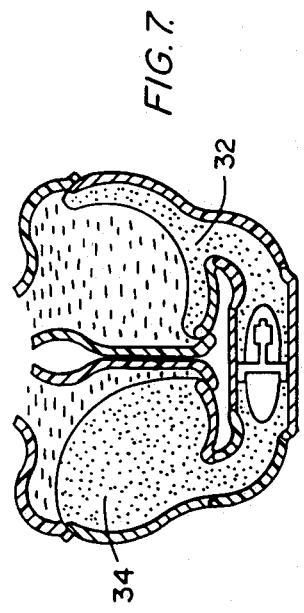
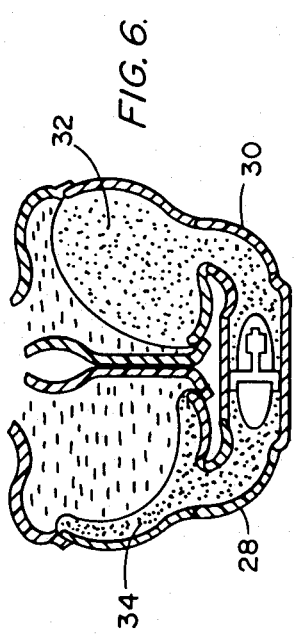
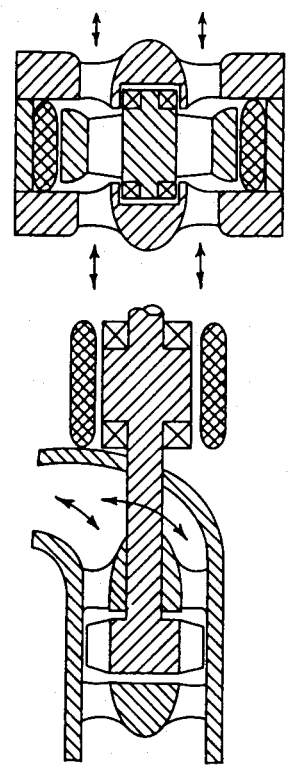
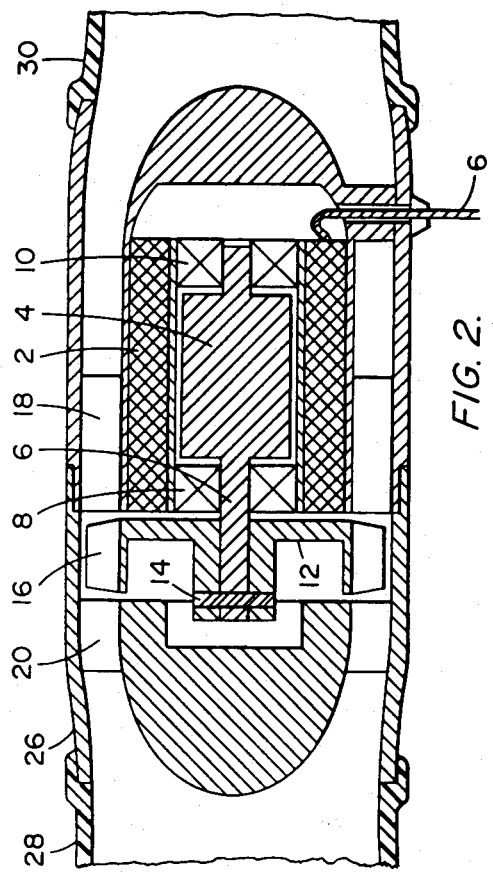
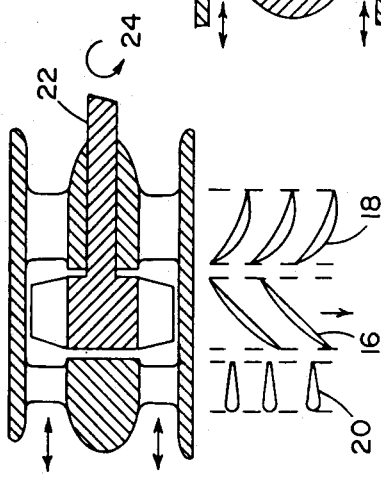

ved by the inventor of the electrohydraulic system
TOTAL ARTIFICIAL HEARTS AND CARDIAC ASSIST DEVICES POWERED AND CONTROLLED BY REVERSIBLE ELECTROHYDRAULIC ENERGY CONVERTERS This invention was made with the support, in the form of a grant, from the Department of Health, Education, and Welfare, and the Government of the United States of America is granted a royalty free non-exclusive license to practice the invention for its own purposes for the duration of any patent which may issue therefrom.

BACKGROUND OF THE INVENTION

Over the last two decades more than one hundred U.S. patents have been issued for inventions involved with artificial blood pumps, energy conversion systems to power these blood pumps, and methods of their control. The prior art includes a wide range of energy sources and devices to utilize these energy sources. Extensive animal experimentation has been conducted using some of these devices and others. Presently the longest length of time during which the entire pumping function of the natural heart has been replaced by an internally implanted blood pump has been 184 days (six months) using the Jarvik-5 type of artificial heart, developed by the inventor of the electrohydraulic system with which this patent deals. The Jarvik-5 type of artificial heart is powered by compressed air and only the blood pump is implanted within the animal. Thus, the drive system which provides for the pumping of the air-driven ventricle is external to the animal. To date the longest animal survival, with an electrically powered total artificial heart, has been achieved using a Scotch yoke mechanism of mechanical diaphragm actuation in a system invented by Nat Bifano and similar to the system disclosed in U.S. Pat. No. 3,896,501. The duration of the longest survival with this electrically-powered heart has been thirty-seven days. These experiments have been conducted in calves, and only once has a total artificial heart been implanted in a human being; this was done by Dr. Denton Cooley and the patient was supported by the artificial heart for a little less than three days, when he received a heart transplant.

Within the past year there have been about 15 cases in which air-driven left ventricular assist devices have been used in human patients. These assist devices have been intended as temporary assist devices and no patients have survived longer than one month after removal of these artificial hearts. None of the artificial hearts disclosed in the prior art has performed well enough to be considered acceptable for permanent replacement of the heart, or for long-term heart assist. Generally, devices which have included energy conversion systems have been very complicated, large, heavy and difficult to adapt to the necessary anatomical constraints. Some, or all, of these problems are apparent with devices such as the following: U.S. Pat. No. 3,842,440 utilizing a linear motor; U.S. Pat. No. 3,791,769 using magnetic forces across the skin; U.S. Pat. No. 3,563,028 using an implantable radioisotope-fueled Stirling Engine; U.S. Pat. No. 3,585,648 using ultrasonic energy; U.S. Pat. No. 3,774,243 using a carbohydrate- or hydrogen-fueled cell in combination with a storage battery to provide electric power for an artificial heart; U.S. Pat. No. 3,633,217 and No. 3,733,616 using electromagnetic actuators. Additional inventions are disclosed in the prior art which use electrohydraulic systems to convert electric power into hydraulic power and thereby actuate a diaphragm or other type blood pump, which have generally been complicated and heavy devices, as are the inventions disclosed in U.S. Pat. No. 3,636,570 and No. 3,048,165. Other electrohydraulic systems are disclosed in U.S. Pat. No. 3,572,979, No. 3,568,214, No. 3,148,624 and No. 3,783,453.

SUMMARY OF THE INVENTION

It is apparent to one skilled in the art of medicine, cardiovascular physiology and circulatory support, that the prior art in the field has not successfully solved numerous problems and resulted in an acceptable, mechanical cardiac support system for long-term, permanent human implantation. In order to achieve this and to be beneficial to a large number of patients, permanently implantable artificial hearts and cardiac assist devices must be successful in six major areas. Additionally, it is recognized that artificial hearts are inferior to the healthy, normal heart, and are likely to remain so. Thus, a perfect device is unattainable and many compromises are necessary to achieve a successful, overall system. It is an object of the present invention to achieve an artificial heart system which will perform successfully in all of the six following categories and which will defer necessary compromises to the areas of lowest priority. In order of priority, these six areas are:

A. Physiologic Function
  1. Acceptable cardiac output
  2. Proper regulation
  3. Acceptable inflow and outflow pressures
  4. Acceptable heart rate
B. Safety (nondamaging to any organ system)
  1. Cardiovascular
     (a) Removability without damage to myocardium (for temporary assist devices)
  2. Hematologic
     (a) Nonthrombogenic or thromboembolic
     (b) Nonhemolytic
     (c) Nondenaturing to proteins
     (d) Other
  3. Pulmonary
     (a) Nonobstructive
  4. Safe as a foreign body
     (a) Freedom from infection (acceptable percutaneous or transcutaneous power transmission)
     (b) Free from production of local pressure necrosis
     (c) Acceptable fit and fixation in position
     (d) Nonproductive of excess local blood or tissue temperatures
C. Durability and Reliability
  1. Use of acceptable biomaterials
     (a) Avoidance of excessive stress concentrations on flexing polymeric components is necessary for long flex life
  2. Mechanical simplicity
  3. Reproducible fabrication methods amenable to excellence of quality control
D. Efficiency
  1. Internal heat production at acceptable levels to be dissipated by the body surface.
  2. Smallest portable electric power supply is desirable
E. Cosmetic and Psychological Acceptability
  1. High confidence level in the device by the patient
  2. Low noise level
  3. Portability (a) Minimum size and weight of any external elements F. Cost

OBJECTS

It is an object of the present invention to provide an electric-to-hydraulic energy conversion system which may be used with a variety of sizes, shapes and types of blood-pumping ventricles.

It is a further object of the present invention to provide an electrohydraulic energy converter in which hydraulic fluid is pumped by an hydraulic pump in a ratio of approximately 1 to 1 with the volume of blood pumped.

It is a further object of the present invention to provide an electrohydraulic energy converter requiring no rotary seals.

It is another object of the present invention to provide an electrohydraulic energy converter which has only one moving part.

It is a further object of the present invention to provide an electrohydraulic energy converting system which has a minimal size and weight and which, when used with a blood pump, can have an overall pump and energy converter specific gravity of 1.

Still another object of the invention is to provide an electrohydraulic energy conversion system which completely surrounds the electric motor with continually moving hydraulic fluid in order to achieve heat dissipation from the motor into the hydraulic fluid.

An additional object of the invention is to provide an electrohydraulic energy converter which can control the pressure wave form of the fluid pumped.

Still another object of the present invention is to provide an electrohydraulic energy conversion system which may be used either to alternately pump the right and left ventricles or to pump the right and left ventricles at the same time.

An additional object of the present invention is to use a high-speed, brushless DC electric motor to power an artificial heart without the necessity of gearing down the motor, which minimizes the size and weight of the motor for a given power output, while maintaining maximum mechanical simplicity.

It is a further object of the invention to provide a method of actuating a diaphragm-type artificial heart in which no pusher plate mechanism or other mechanism is required between the right and left ventricle, thus simplifying adaption of the ventricles to the human anatomy.

It is a further object of the present invention to provide an electrohydraulic energy conversion system having no contacting mechanical parts other than a single set of bearings, thus reducing problems of mechanical wear and increasing reliability and durability.

It is an additional object of the present invention to provide a total artificial heart or cardiac support system which can be totally implanted with the exception of an external electrical power source such as a battery.

It is another object of the present invention to provide an artificial heart system which utilizes modern microcircuit electronics to commutate the electric motor and to monitor and control the performance of the device throughout the cardiac cycle.

A preferred embodiment is disclosed in connection with reference to the FIGURES in which:

FIG. 1 is a longitudinal section through an axial flow pump, also diagramming the profiles of the impeller and stator blading.

FIG. 2 is a longitudinal section through an artificial heart electrohydraulic energy converter system utilizing a brushless DC motor and an axial flow pump.

FIG. 3 is a simplified longitudinal section of an electrohydraulic energy converter for an artificial heart having an axial flow pump impeller with a hub diameter larger than the outside diameter of the brushless DC motor.

FIG. 4 is a simplified schematic, longitudinal section of an electrohydraulic energy converter for an artificial heart having an axial flow pump impeller smaller than the outside diameter of the brushless DC motor and indicating the necessity for the hydraulic fluid to turn an angle in this layout.

FIG. 5 is a simpligied schematic, longitudinal section, of an electrohydraulic energy converter having an axial flow pump impellor which is contained within a bore in the rotor of the brushless DC motor.

FIG. 6 is a simplified schematic, sectional view, of an electrohydraulic energy converter using an axial flow pump adapted to actuate a diaphragm-type total artificial heart. FIG. 6 indicates the extreme position of hydraulic fluid when one of the two blood ventricles is completely emptied.

FIG. 7 is a similar view of an artificial heart, as illustrated in FIG. 6, shown when the hydraulic fluid has been pumped to the opposite side.

ENERGY CONVERTER

Figure 8:
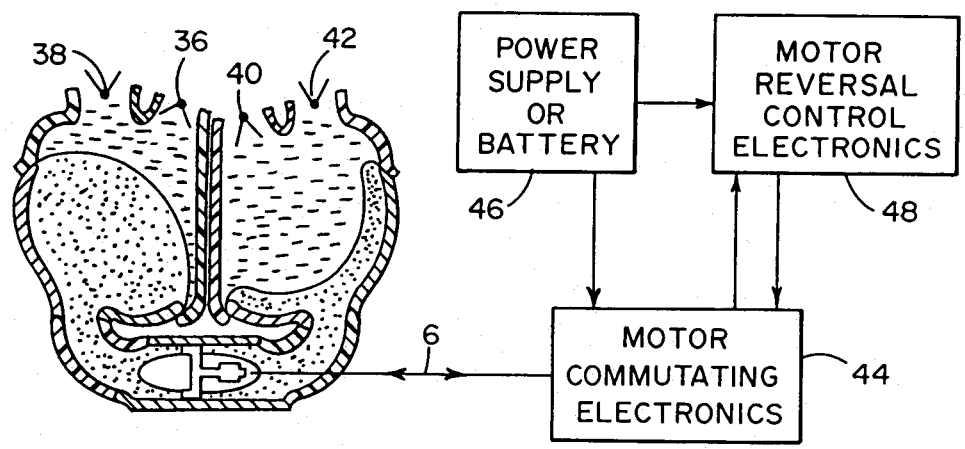
FIG. 8 is a diagrammatic representation of the entire system including energy converter, artificial ventricle, motor, commutating electronics, power supply and motor reversal control electronics.

The preferred embodiment of the present invention combines an axial flow pump with a brushless DC motor commutated according to information gained by monitoring the back EMF of the motor windings. Many types of motors are known and since this artificial heart may be powered by a battery, a DC-type of motor is most desirable. Brush-type DC motors do not provide long enough durability for permanently implantable devices since the brushes wear out. Additionally, it is desired to run the motor submerged in the hydraulic fluid and to have no rotary seals. While a few fluids are known which permit operation of brush-type motors submerged in these fluids, the situation is nonetheless suboptimal and the choice of hydraulic fluid would be greatly limited. It is very desirable to use water for the hydraulic fluid since is is of low viscosity and low specific gravity and is nontoxic in the event that a small amount diffuses through the diaphragm into the blood. If the water is conductive, brush-type motors cannot be operated when submerged therein. For these and other reasons it is highly desirable to use brushless-type DC motors. Many methods of commutating brushless DC motors are known. These often include the use of a device to sense the motor rotor position. Such devices include permanent magnet generators, Hall devices, eddy current devices, reluctance devices, optical sensors, capacitance devices, resolvers and radiation devices; however, use of any of these devices with a motor implies increased complexity of the mechanical parts and often requires additional inertia as a result of attaching a sensing device onto the motor rotor. Means for selectively controlling the speed of the motor may comprise, for example, brushless DC motors which operate using information gained from monitoring the back EMF in the windings to sense the rotor position and control commutation have been developed. An example of such a motor is disclosed in U.S. Pat. No. 4,027,215.

In addition to the mechanical simplicity described in the patent just mentioned, the motor disclosed therein also has the capability of being accelerated and decelerated extremely rapidly. FIG. 2 shows a motor of this type incorporated into the energy converter system. The windings and laminations are generally indicated at 2. The rotor 4 of the motor, comprises permanent magnets fixed to a shaft 6. These magnets are preferentially rare earth cobalt with the existing state of the art in magnet materials; however, any magnetic material which has a great enough magnetic flux and is noncorroding in the hydraulic fluid used, and which does not demagnetize when high current spikes are applied to the windings, is acceptable. These are properties of rare-earth cobalt magnets. Still referring to FIG. 2, the shaft 6 of the brushless DC motor is supported by a pair of bearings, 8 and 10. The design of these bearings must permit them to accept axial thrust as well as radial load. Bearings used may be ball-bearings, or simple sleeve bearings may be used with special design and special materials to permit adequate durability under the high-speed and rapidly reversing cycle. An example of such a type of bearing, material and design is Graphitar, produced by the Wickes Corporation of Saginaw, Mich. An example of a sophisticated thrust bearing using this material is given in their 1976 catalog:

This sophisticated thrust bearing operates in a nuclear reactor where it can never be reached for maintenance or replacement. The rotating member which is supported on this Graphitar bearing stops and starts frequently . . . the toughest kind of application for bearing material. Graphitar was selected for this application because it not only had one of the lowest coefficients of friction of all engineering materials but it has the unique characteristic of exhibiting almost no difference between its static and sliding coefficients. This attribute is a particular value in the thrust bearing because it minimizes start-up torque and permits a full lubricant film to be established almost instantly as the rotating member begins to move.

Additionally, Graphitar may be an excellent bearing material because its best lubricant is water. Still referring to FIG. 2, we see the rotor of the axial flow pump, 12, fixed directly to the shaft of the motor by means of pin 14. The rotor has blades which act against the fluid, generally indicated at 16. The axial flow pump also uses stator blades 18 and 20 to convert rotational fluid flow caused by the impeller into generally axial flow.

FIG. 1 shows a diagram of a typical axial flow pump in which the impeller is driven by shaft 22. With rotation as indicated at 24, the fluid flow is as indicated in FIG. 1. If the direction of rotation of the impeller is reversed, the fluid flow is also reversed. The axial flow pump is the preferred type of reversible pump for the preferred embodiment of the present invention. Generally, axial flow pumps are high-volume low pressure pumps designed to operate at high speeds. Generally these pumps are produced in huge sizes and are used in such situations as in large water projects such as aqueducts. Presently the smallest commercially available axial flow pumps have rotor diameters of approximately six inches and produce flows of about 1,000 gallons per minute. These, and larger pumps, when operating under design conditions, that is, at the best pressure heads and proper speed of rotation, can achieve efficiencies in excess of 90 or 95%. Generally this type of pump is not made in small sizes because the manufacture of the blading is difficult and expensive and because the tolerances required, particularly the clearance gap between the tip of the rotors and the inside of the chamber in which the rotors turn, must be very close. Centrifugal pumps are simpler and less expensive to produce and do not require these close tolerances; however, centrifugal pumps do not reverse the direction of flow when the direction of rotation of the impeller is reversed.

An additional advantage of the axial flow type of pump is that for a given flow, the inertia of the impeller is minimized. Also, there are no contacting parts other than the bearings, such as are found with positive displacement pumps such as gear pumps. Other types of reversible pumps without contacting parts exist, such as the peripheral pump; however, no other device known to the inventor combines the reversibility feature with the low inertia and smooth, efficient, balanced operation of turbomachinery found in the axial flow pump which is required for the rapidly reversing artificial heart application. An additional advantage of an axial flow pump is its smooth, quiet operation and durability. Additionally the pump can be designed so that with the given maximum power, available from the brushless motor with which it is combined, the system cannot generate excessive pressure of a level which would be sufficient to rupture the diaphragms. Thus, the pump would stall at a given pressure, although the rotor continues to turn at relatively high speeds. Again, referring to FIG. 2, the housing of the axial flow pump is indicated at 26 and the tubes used to connect the hydraulic fluid to the artificial ventricles or fluid reservoir sacks are indicated at 28 and 30. FIGS. 3, 4 and 5 diagram the different layouts which may be used with the axial flow pump reversing energy converter.

FIG. 3 shows a pump impeller of slightly larger diameter than the outside diameter of the brushless DC motor. With this arrangement a straight flow path of hydraulic fluid is achieved. The rotor of the motor is internal to the laminations and windings, which is the most desirable situation in order to achieve the highest ratio of motor power to motor rotor inertia. FIG. 4 shows a situation in which the hub diameter of the rotor of the pump is smaller than the outside diameter of the motor and which requires the hydraulic fluid flow to turn a bend. This layout has the advantage that the impeller inertia may be minimized and the ratio of pump impeller blade outside diameter to pump impeller hub diameter may be optimal. This type of impeller design may require twisted blading and may give the highest pump efficiency. A similar ratio of pump impeller outside diameter to pump impeller hub diameter can be achieved with layouts shown in FIG. 5. In this layout the rotor of the motor carries the magnets and has a hollow bore in which the pump rotor is nested. Although this layout is quite compact and permits a straight flow-through path while obtaining the desirable relationships of pump hub diameter to outside diameter, the motor of the rotor has a much higher inertia per unit power than does the rotor of the motors shown in either FIG. 3 or FIG. 4. Thus the scheme shown in FIGl. 5 is not preferred because of the importance of inertial effects on rapid reversal. The method of function of the reversing energy converter to actuate a diaphragm-type of total artificial heart is illustrated in FIGS. 6 and 7. Generally an hydraulic fluid is alternately pumped from one chamber, where it actuates a diaphragm to another chamber, where it actuates another diaphragm. This reversal of flow occurs when the motor and pump are reversed and thus provides alternating fluid power to the right and left side of the total artificial heart, with a system of maximum mechanical simplicity. The volume of hydraulic fluid pumped is approximately the same as the volume of blood pumped. In the event that the soft shell-type of artificial ventricle is used to regulate the blood flow (see U.S. Pat. No. 3,641,591) the volume of hydraulic fluid pumped during each systole may exceed the volume of blood ejected from the ventricle.

In FIG. 6 the hydraulic fluid is indicated by the dotted stippling and occupies a chamber behind the diaphragm of the left ventricle, indicated at 32; two hydraulic fluid conduits, generally indicated at 28 and 30; and a small part of the right ventricular hydraulic fluid chamber, indicated at 34. The blood occupies the ventricle as indicated by the dashed line stippling. In FIG. 6 the right ventricle is shown at end diastole and the left ventricle is shown at end systole. FIG. 7 illustrates the situation after the pump has been reversed and the cycle is nearly complete. Now the left ventricle hydraulic fluid chamber 32 is practically emptied of hydraulic fluid, as the left ventricle is in the end diastolic position. The inflow and outflow valve to the right and left ventricles are diagrammed in FIG. 8, as indicated by right inflow 36 right outflow 38, left inflow 40, left outflow 42. Still referring to FIG. 8, the brushless DC motor is connected to the power supply and electronics by means of an electric cable, 6. This cable transmits power into the motor and also receives information about the position of the motor rotor via the back EMF. The motor commutating electronics, generally indicated at 44, senses the position of the rotor and switches the power on and off in the different windings of the motor at the appropriate times. The power supply, which may be a battery, is generally indicated at 46. Motor reversal control electronics comprising a fixed memory device is generally indicated at 48. The motor reversal control electronics contain logic which recognizes the direction of rotation of the motor, the motor speed and the torque the motor is applying to the pump. The reversal control electronics command the motor to reverse at the appropriate time. Additionally, the logic determines that power to the motor should be shut off, allowing the pump to coast, or that dynamic breaking of the motor should be occurring, and suitably commands the motor commutating electronics to do this. The motor reversal control electronics may utilize feedback control from pressure sensors in the hydraulic fluid or may recognize when the diaphragm has reached full extension by a build-up of pressure and the resulting change in the power requirements to the motor.

Additionally, the motor reversal control electronics may receive external commands such as a signal picked up from the electrocardiogram or may refer to a stored data bank of information to determine the instantaneous motor direction and speed and requirement for application for power.

Figure 9:
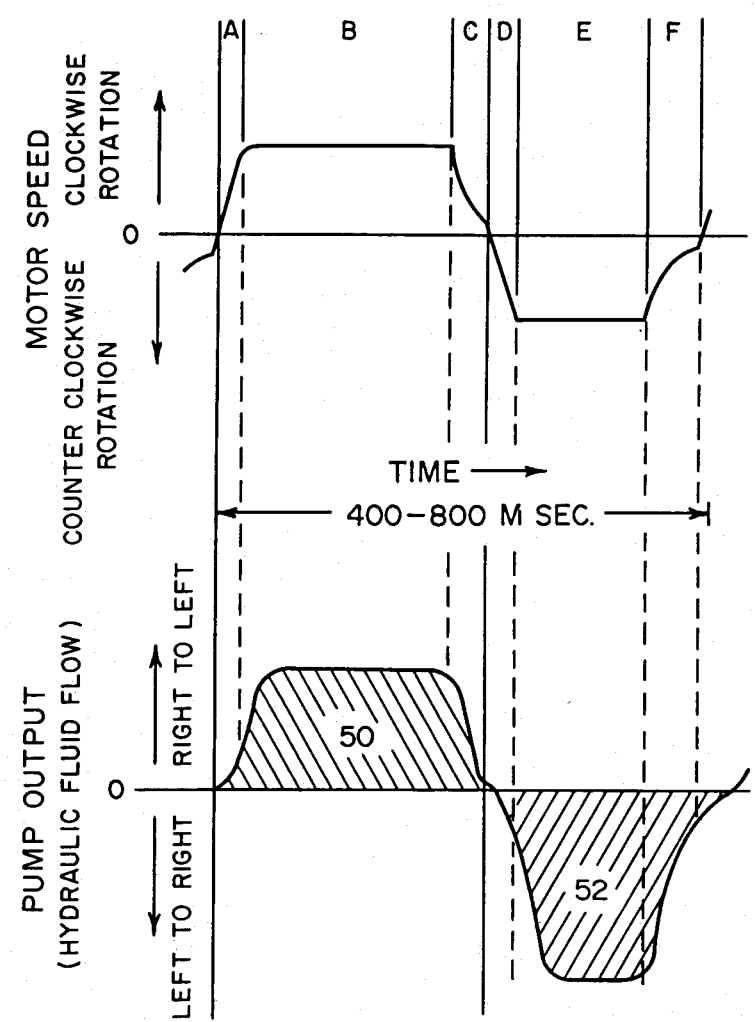
FIG. 9 is a diagram of the reversing cycle indicating the rotation of the motor and pump impeller, first in the clockwise direction, then in the counter-clockwise direction, and indicating the reversal of hydraulic flow which occurs with reversal of the pump.

FIG. 9 illustrates a simple operating cycle of the reversing electrohydraulic energy converter. The cycle which for normal heart rates of 60 to about 120 beats per minute has an overall cycle duration of about 400 to 800 miliseconds, is divided into six segments:

Segment A represents acceleration of the motor in one direction, let us presume clockwise. As the motor and thus pump impeller are accelerated the pump output, which is shown as the hydraulic fluid flow, increases as illustrated in the lower portion of the diagram of FIG. 9. It is presumed that the hydraulic fluid flow will lag the pump rotor speed somewhat, which can be observed by a careful comparison of the Segment A of the motor speed and the pump output curves. During Segment B the motor speed is held at a constant optimal value, as determined by the motor reversal control electronics. At the beginning of Segment C the motor is either allowed to coast to its lower speed or is dynamically braked. During Segments A, B and C hydraulic fluid is pumped from one side of the heart to the other, as diagrammed here from right to left. When the beginning of Segment D is reached the motor reversal control electronics command the motor to reverse. The final deceleration of the motor in the clockwise direction occurs and the motor is reaccelerated in the counter-clockwise direction. Then a plateau motor speed, as determined by the motor reversal control electronics, is held during Segment E. At the beginning of Segment F the motor is again allowed to begin deceleration by shutting off power or by dynamic braking. The end of Segment F corresponds to the beginning of Segment A. During the intervals D, E and F hydraulic fluid flow in the device is reversed and now the fluid is pumped from left to right. On the average, over many heart beats, the hydraulic fluid flow pumped from right to left, indicated by the area under the curve, 50, must equal the hydraulic fluid flow pumped from left to right, as indicated under the curve 52; however, on a strictly beat-to-beat basis over one cycle these flows must not necessarily be equal. It is apparent to one skilled in the art of feedback control that numerous control mechanisms are possible without departing from the basic principles of operation.

The motor reversal control electronics must only reverse the motor twice for each complete cycle. This could be accomplished with a simple, fixed rate timing device and fixed duration of timing allowable for the various Segments A, B, C, D, E and F. Additionally, a fixed speed could be selected for Segments B and E; however, the optimally performing artificial heart may require a variation and heart rate, and thus a variation in time of the overall cycle. Also, when the blood pressure against which the ventricles must eject blood changes, the power requirements to do this also change. The reversal electronics preferentially can recognize the changes in outflow pressure and provide appropriate motor speed to achieve optimal blood flow in the period available. Additionally, the control electronics may preferentially sense complete filling and complete emptying of one or both of the ventricles and command reversal and pump speed accordingly. Additionally more sophistication of the motor reversal control electronics may permit the power to the motor to be shut off at a time when the inertia in the pump impeller and motor rotor have the ability to do useful work in pumping fluid and thus part of the power used to accelerate this inertia may be recovered as useful hydraulic power. Many additional refinements of the motor reversal control system may be used to either optimize the efficiency of the overall system or to provide another useful function, such as control of the arterial pressure waveform generated by the pump. Additionally, the output of the axial flow pump is somewhat sensitive to the filling pressure and with proper reversal control logic, motor power can be shut off prior to complete filling of one of the blood chambers. If this is done appropriately the blood filling pressure can force the diaphragm further and can force additional hydraulic fluid through the pump and thus determine the degree of filling. This in turn determines the stroke volume of a particular beat and this principle may be used to control the cardiac output. This is analagous to the Frank Starling's mechanism of control of output of the natural heart according to the filling pressure.

Figure 11:
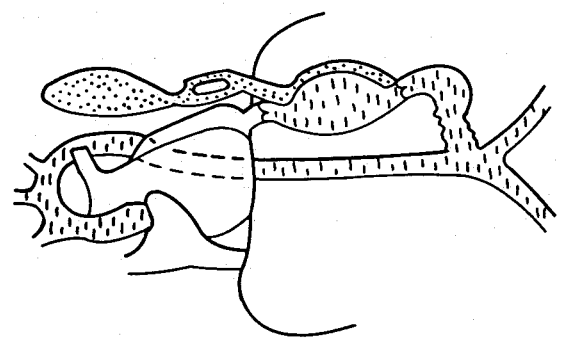
FIG. 11 is a diagrammatic representation similar to FIG. 10 in which the blood pump is shown in the diastolic position and the hydraulic fluid in the chest cavity is shown maximally filled.
Figure 10:
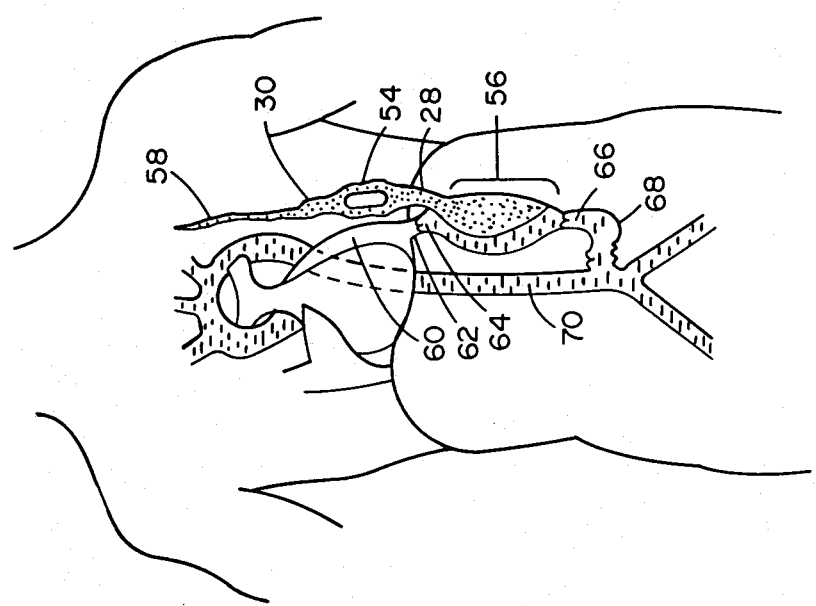
FIG. 10 is a simplified diagrammatic representation of the electrohydraulic energy system used to power a left ventricular assist device in which the blood pump is placed abdominally below the patient's diaphragm and the hydraulic fluid reservoir is placed in the chest cavity of the patient. In this figure the blood pump is shown in the end systolic position.
Figure 12:
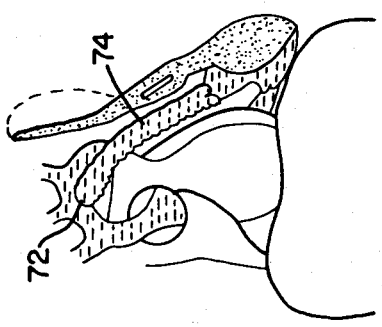
FIG. 12 is a diagrammatic representation of the reversing electrohydraulic energy converter used with a left ventricular assist device in which the blood pump is implanted in the thoracic cavity.

FIG. 10 diagrams a left ventricular assist device utilizing the electrohydraulic energy converter generally indicated at 54. The conduit 28, connecting one of the sides of the axial flow pump to the left ventricular assist ventricle generally indicated at 56, crosses the patient's diaphragm. A second hydraulic fluid conduit 30, connects the opposite side of the axial flow pump to a fluid reservoir bag 58, located in the thoracic cavity of the patient. This fluid reservoir bag is preferentially constructed with a large surface area, so that a small excursion of the two walls of the bag is all that is necessary to accommodate a relatively large volume of fluid. The artificial ventricle indicated generally at 56 is connected to the apex of the patient's natural left ventricle 60, by means of an apical cannula 62. This provide the blood inflow to the artificial ventricle. The inflow valve is indicated at 64 and the outflow valve of the blood pump is indicated at 66. An outflow cannular indicated generally at 68 connects the artificial ventricle to the patient's abdominal aorta 70. FIG. 10 indicates this system during artificial ventricle end systole. When the pump has been reversed and the hydraulic fluid has been pumped into the reservoir bag 58, in the thoracic cavity, the blood pump is in the end diastolic position shown in FIG. 11. The hydraulic fluid reservoir bag is deliberately located in the thoracic cavity to permit changes in volume to be accomodated through the compliance of the lungs. A slightly different anatomical placement, in which the energy converter system 54, is placed below the diaphragm with the blood pump while the hydraulic fluid reservoir is maintained in the thoracic cavity, is also possible. Additionally the blood pump energy converter and reservoir bag may all be placed in the thoracic cavity, as illustrated in FIG. 12. Here the outflow of the blood pump is connected to the patient's ascending aorta at 72 by means of an outflow graft 74. An additional, practical method of connecting this left ventricular assist device would be to place the blood pump abdominally, as in FIG. 10, but provide an outflow graft which re-enters the thoracic cavity and connects the outflow of the blood pump to the thoracic ascending aorta. The important principle which this electrohydraulic energy converter makes possible is a versatile system which can be anatomically adapted in several ways while retaining the ability to maintain the compliant hydraulic fluid reservoir within the chest cavity. This same anatomic versatility is maintained if the system is used as a total artificial heart. In this case the ventricles would be placed in the position that had previously been occupied by the removed, natural ventricles. Placement of the energy converter itself somewhat to the side of the ventricles permits the most direct anatomical connection of the artificial ventricles to the great vessels. In previous artificial heart designs actuated by pusher plates and other mechanisms, it has often been necessary to place an actuating device between the left and right ventricular pumping chambers. The use of the hydraulic pumping fluid permits maximum versatility in the design of the ventricles itself and does not encumber a central area of the device with mechanisms, which makes anatomic fitting difficult.

Additionally, the hydraulic fluid is able to distribute the forces and stresses quite uniformly on a blood pumping diaphragm and permits the design of nongeometric diaphragmatic surfaces. The design of an artificial heart with unusually shaped diaphragms is much more difficult if pusher plate actuation is used.

The energy converter disclosed in this patent may also be used to power a total artificial heart in which both the right and the left ventricles have systole occurring simultaneously and also both the right and left ventricles have diastole occurring simultaneously. In this situation it is necessary to provide an additional hydraulic fluid reservoir chamber. Also, two energy converter systems may be used, one to provide pumping power to the left side of the heart, and the other to provide pumping power to the right side of the heart. If each side is provided with an independent hydraulic fluid reservoir, the output of the right and left artificial ventricles can be independently adjusted and balanced if appropriate feedback and motor reversal control logis is provided. Balance of the right and left ventricle can also be achieved using a single electrohydraulic energy converter alternately pumping from the right to the left. However, in this situation the control of right ventricular and left ventricular output is not entirely independent and additional means to balance the outputs may be required, such as providing a stiffer ventricular housing on the left side and a right ventricular inflow valve having a greater regurgitation and back leakage than the left ventricular inflow valve.

Having described my invention it is apparent that additional embodiments, configurations and reversal control can be used without departing from the scope of the invention. For example, other methods of detecting the rotor position of the motor and commutation may be used. Also, other types of reversible hydraulic pumps could be used if they meet the requirements of high speed operation, low inertia and acceptable durability. It can therefore be appreciated that a variety of modifications can be made without departing from the scope of the invention.

Therefore, what I claim and intend to secure by letter patents of the United States is:

1. An electric-to-hydraulic energy conversion system to actuate and control a diaphragm, sac or axisymmetric blood pump for use in a total artificial heart or cardiac assist system comprising:
    a reversible hydraulic pump having stator, diffusor elements, and an impellor, and said pump having a high ratio of flow to impellor inertia,
    a reversible brushless DC motor having a high ratio of power to inertia, said motor having a rotor and stationary elements,
    a shaft to which both the impellor of the pump and the rotor of the motor are fixed,
    a housing supporting both said stator and diffusor elements of the pump and the stationary elements of the motor,
    bearings mounted in the housing supporting the assembly of shaft, motor rotor, and pump impellor for rotation,
    means for reversing said motor to alternately cause systolic and diastolic action of the artificial heart, and
    means for controlling said motor reversing means.

2. An electric-to-hydraulic energy conversion system as defined in claim 1, in which the hydraulic fluid pump is an axial flow pump.

3. An electric-to-hydraulic energy conversion system as defined in claim 1, in which the brushless DC motor is commutated by the back EMF of the motor.

4. An energy converter as defined in claim 1, in which the volume of blood adapted to be ejected from the artificial ventricle during systole is substantially the same as the volume of fluid pumped by the reversible hydraulic pump.

5. A cardiac assist system actuated by an electrohydraulic energy converter as defined in claim 1, in which the blood pump is adapted to be placed in the abdomen of a patient and a compliant reservoir sack is adapted to be placed in the chest with the energy converter positioned between said blood pump and said sack.

6. A total artificial heart having a right and left ventricle actuated by an electrohydraulic energy converter as defined in claim 1, in which the hydraulic fluid is alternately pumped from the right to the left ventricle and vice versa, and in which blood is adapted to be alternately pumped out of the right and left ventricles.

7. An energy conversion system as defined in claim 1 in which the motor reversal controlling means is a fixed memory device.

8. An energy conversion system as defined in claim 1 in which the motor reversal controlling means is operated under control of feedback signals derived from differences in torque of the motor.

9. An energy conversion system as defined in claim 1 in which the motor reversal controlling means is operated under control of pressure transducers.

10. An energy conversion system as defined in claim 1 in which the motor reversal controlling means is operated under control of electrocardiographic signals.

11. An energy conversion system as defined in claim 1 including means for selectively controlling the speed of the motor.

* * * * *